(12) United States Patent
Rombach et al.

(10) Patent No.: US 10,463,473 B2
(45) Date of Patent: Nov. 5, 2019

(54) ACCOMMODATING INTRAOCULAR LENS WITH VARIABLE CORRECTION

(75) Inventors: Michiel Christiaan Rombach, Breda (NL); Aleksey Nikolaevich Simonov, Delft (NL)

(73) Assignee: Akkolens International B.V., Breda (NL)

( * ) Notice: Subject to any disclaimer, the term of this patent is extended or adjusted under 35 U.S.C. 154(b) by 1558 days.

(21) Appl. No.: 12/518,458

(22) PCT Filed: Dec. 13, 2007

(86) PCT No.: PCT/EP2007/063871
§ 371 (c)(1),
(2), (4) Date: Dec. 16, 2009

(87) PCT Pub. No.: WO2008/071760
PCT Pub. Date: Jun. 19, 2008

(65) Prior Publication Data
US 2010/0094413 A1 Apr. 15, 2010

(30) Foreign Application Priority Data
Dec. 13, 2006 (EP) .................................. 06125992

(51) Int. Cl.
*A61F 2/16* (2006.01)
(52) U.S. Cl.
CPC .......... *A61F 2/1613* (2013.01); *A61F 2/1632* (2013.01); *A61F 2/1648* (2013.01)
(58) Field of Classification Search
CPC ..... A61F 2/1613; A61F 2/1648; A61F 2/1632
See application file for complete search history.

(56) References Cited

U.S. PATENT DOCUMENTS

| | | |
|---|---|---|
| 3,305,294 A | 2/1967 | Alvarez |
| 3,583,790 A | 6/1971 | Baker |
| 4,650,292 A | 3/1987 | Baker et al. |
| 6,609,793 B2 | 8/2003 | Norrby et al. |

(Continued)

FOREIGN PATENT DOCUMENTS

| | | |
|---|---|---|
| WO | 0180781 A1 | 11/2001 |
| WO | 0185067 A2 | 11/2001 |

(Continued)

OTHER PUBLICATIONS

Search Report (partial) for European Patent No. 06 12 5992; dated Jul. 3, 2007.

(Continued)

*Primary Examiner* — Leslie Lopez
(74) *Attorney, Agent, or Firm* — The Webb Law Firm

(57) ABSTRACT

An accommodating intraocular lens with variable optical power, comprising at least two optical elements, at least one of which is movable relative to the other in a direction perpendicular to the optical axis, wherein the optical elements form a lens with different optical power at different relative positions of the optical elements. At least two of the optical elements of the lens comprise at least one additional optical correction surface, which correction surfaces are adapted for simultaneous variable correction of one or more optical aberrations of the natural eye in which the degree of correction depends on the relative position of the optical elements.

4 Claims, 3 Drawing Sheets

(56) References Cited

U.S. PATENT DOCUMENTS

| | | |
|---|---|---|
| 6,705,729 B2* | 3/2004 | Piers et al. .................... 351/246 |
| 2002/0122153 A1* | 9/2002 | Piers .................... A61B 3/1015 |
| | | 351/212 |
| 2005/0027354 A1* | 2/2005 | Brady .................... A61F 2/1613 |
| | | 623/6.31 |
| 2006/0041307 A1 | 2/2006 | Esch et al. |
| 2008/0046076 A1* | 2/2008 | Rombach .................... 623/6.34 |

FOREIGN PATENT DOCUMENTS

| | | |
|---|---|---|
| WO | 03032825 A1 | 4/2003 |
| WO | 2005084587 A2 | 9/2005 |
| WO | 2006025726 A1 | 3/2006 |
| WO | 2006118452 A1 | 11/2006 |
| WO | 2007015640 A1 | 2/2007 |

OTHER PUBLICATIONS

Cheng et al.; A population study on changes in wave aberrations with accommodation; Journal of Vision; 2004; pp. 272-280; vol. 4.
Pomerantzeff et al.: Wide Angle Optical Model of the Human Eye; Annals of Ophthalmology; Aug. 1971; pp. 815-819.
Pomerantzeff et al.; Wide-Angle Optical Model of the Eye; Advances in Diagnostic Visual Optics; Proceedings of the Second International Symposium; Oct. 23-25, 1982; pp. 12-21; Tucson, Arizona.
Search Report and Written Opinion for International Patent Application No. PCT/EP2007/063871; dated Jul. 21, 2008.

\* cited by examiner

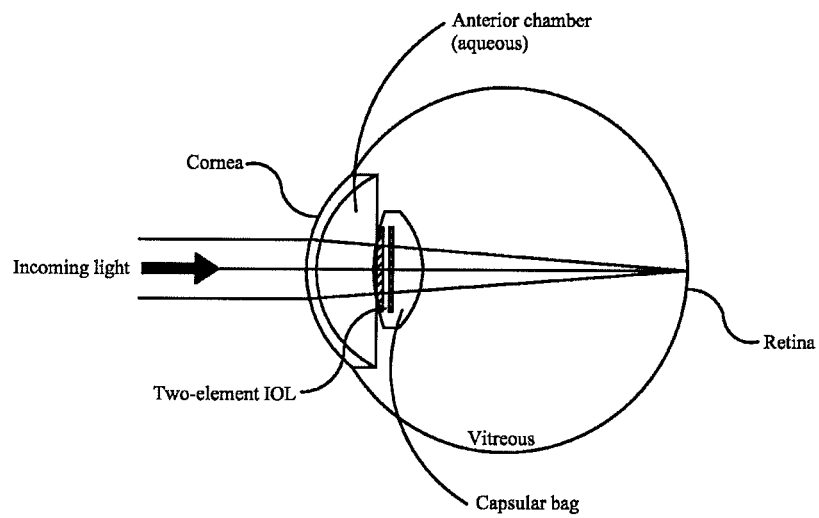
PRIOR ART FIG. 1
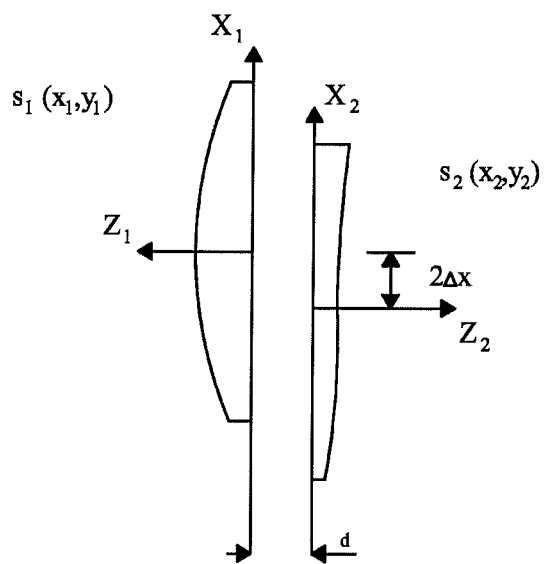
FIG. 2

ACCOMMODATING INTRAOCULAR LENS WITH VARIABLE CORRECTION

PRIORITY CLAIM OR CROSS REFERENCE TO RELATED APPLICATIONS

This patent application is a U.S. National Phase of International Patent Application No. PCT/EP2007/063871, filed Dec. 13, 2007, which claims priority to European Patent Application No. 06125992.5, filed Dec. 13, 2006, the disclosures of which are incorporated herein by reference in their entirety.

FIELD

The present disclosure relates to an accommodating intraocular lens with variable optical power.

BACKGROUND

Lenses with variable optical power with optical components which shift perpendicular to the optical axis to vary the optical power have been first described by Louis Alvarez in 1967 (U.S. Pat. No. 3,305,294). Such lenses with variable optical power comprise two optical elements mutually movable in a direction perpendicular to the optical axis and wherein the optical elements have such a form that the combination of the two optical elements results in a lens with different optical powers at different relative positions of the optical elements. The form of the optical elements is described as a cubic element best represented by the basic formula $$z = \frac{A}{2}\left(\frac{x^3}{3} + xy^2\right)$$

which formula forms the base of U.S. Pat. No. 3,305,294 and will be set forth below.

This optical principle was later extended to include rotating designs, semi-rotating designs, designs in which only one optical element has to be shifted and designs with additional fifth-order surfaces for correction of spherical aberrations. These variations are described in U.S. Pat. Nos. 3,583,790; 3,305,294; and U.S. Pat. No. 4,650,292 which are incorporated herein by reference in their entirety.

By far the majority of intraocular lenses (hereinafter referred to as "IOLs") which are implanted in the eye are standard monofocal IOLs or, in lesser numbers, multifocal IOLs with multiple but fixed foci. At present, several promising models of IOLs which can focus the eye driven by natural means (hereinafter referred to as "AIOLs") are in development in addition to the fixed focus and multifocal IOLs. All these IOLs and AIOLs replace the natural crystalline lens in the human eye to treat, for example, cataracts of the eye or to treat general accommodative and refractive errors of the eye in absence of cataract. AIOLs with shifting cubic optical elements and variations thereon have been described in International Patent Publication Nos. WO 2005/084587 and WO 2006/118452, which are incorporated herein by reference in their entirety.

Such intraocular lenses with shifting optics can produce various undesired variable aberrations depending on, for example, the distribution of optical surfaces, their mutual degree of movement and other aspects of the optical design. For example, a lens of fixed diopter power can be distributed over two shifting optical elements of an accommodating intraocular lens resulting in a variable astigmatism and coma once the elements shift. Such undesired aberrations of the lens itself can be variably corrected according to the inventions set out below in addition to correction of various undesired variable aberrations of the eye itself.

Clearly, it is desirable to have a lens with variable focal length, of which the focusing is driven by natural means, e.g., the ciliary muscle of the eye, to provide the patient with spectacle-free life. However, the human eye does not only defocus at contraction/relaxation of the ciliary muscle but also shows a number of variable aberrations of higher orders which change along with defocus. For purposes of the present disclosure, these aberrations can be defined as "variable accommodation-induced aberrations" and are additional to fixed aberrations of the eye.

Constant and lower-order ocular aberrations of the natural eye can be successfully corrected by ophthalmic lenses, for example, by spectacles or contact lenses with sphero-cylindrical optics, laser treatment of the cornea, etc. Variable accommodation-induced aberrations are well studied and are of significant importance for human vision, but current ophthalmic lenses such as spectacles, contact lenses and IOLs cannot address these variable aberrations. An ideal AIOL, should correct for these variable accommodation-induced aberrations during the focus/defocusing process. In the latter AIOLs the defocus term can be corrected, but an option to correct for other aberrations is likely impossible to be implemented on spherical surfaces moving along the optical axis.

Consequently, the present invention offers the possibility to correct aberrations caused by the natural eye and to correct variable aberrations caused by the intraocular lenses themselves, on their own or in combination such that the combination of fixed diopter powers is distributed over the two optical elements such that the combination of the fixed optical powers is constant regardless of the position of the two optical elements relative to each other.

SUMMARY

The present disclosure describes several exemplary embodiments of the present invention.

One aspect of the present disclosure provides an accommodating intraocular lens with variable optical power, comprising at least two optical elements, at least one of which is movable relative to the other in a direction perpendicular to the optical axis, wherein the optical elements have such a form as to result in a lens with different optical power at different relative positions of the optical elements, and wherein at least two of the optical elements of the lens comprise at least one additional optical correction surface which correction surfaces are adapted for simultaneous variable correction of one or more optical aberrations in which the degree of correction depends on the relative position of the optical elements.

Another aspect of the present disclosure provides a method for applying an accommodating intraocular lens to a human eye, comprising a) preparing a lens having at least two optical elements, at least one of which is movable relative to the other in a direction perpendicular to the optical axis, and wherein the optical elements form a lens with different optical power at different relative positions of the optical elements; and b) implanting the lens into the human eye, wherein the variable aberrations of the cornea are measured during the accommodation process by corneal topography, wherein the properties of correction surfaces of the optical elements are calculated from the measured aberrations, and wherein the preparation of the optical elements includes the provision of correction surfaces which are adapted for simultaneous variable correction of one or more optical aberrations in which the degree of correction depends on the relative position of the optical elements.

A further aspect of the present disclosure provides a system for preparing an implantable accommodating intraocular lens, wherein the intraocular lens comprises at least two optical elements, at least one of which is movable relative to the other in a direction perpendicular to the optical axis; wherein the optical elements form an intraocular lens with different optical power at different relative positions of the optical elements, and wherein at least two of the optical elements of the intraocular lens comprise at least one additional optical correction surface, which correction surfaces are adapted for simultaneous variable correction of one or more optical aberrations in which the degree of correction depends on the relative position of the optical elements, the system comprising a) means for measuring the variable aberrations of the eye; b) means for calculating the correction surfaces in dependence of the measured aberrations; and c) means for preparing the optical elements including the calculated correction surfaces.

BRIEF DESCRIPTION OF THE DRAWINGS

Various aspects of the present disclosure are described hereinbelow with reference to the accompanying figures.

FIG. 1 is a schematic view of the components of the wide-angle model eye developed by Pomerantzeff (Wide angle optical model of the human eye, Ann. Ophthalmol. 3, 815-819, 1971; Wide-angle optical model of the eye, in Advances in Diagnostic Visual Optics, Breinin and Siegel, eds., Springer-Verlag, Berlin, 1983) implanted with a two-element lens described in this reference. This Pomerantzeff model of the eye was used for calculations to generate the example presented herein.

FIG. 2 is a schematic view of an AIOL according to one aspect of the present disclosure with two cubic surfaces on two optical elements, wherein each optical element is a single piece, for accommodation (focus/defocus), one parabolic lens on only the anterior element for a fixed basic focus and additional fifth order surfaces on both elements to correct for increasing spherical aberration which occurs along with variation in focal distance.

DETAILED DESCRIPTION

Figure 3:
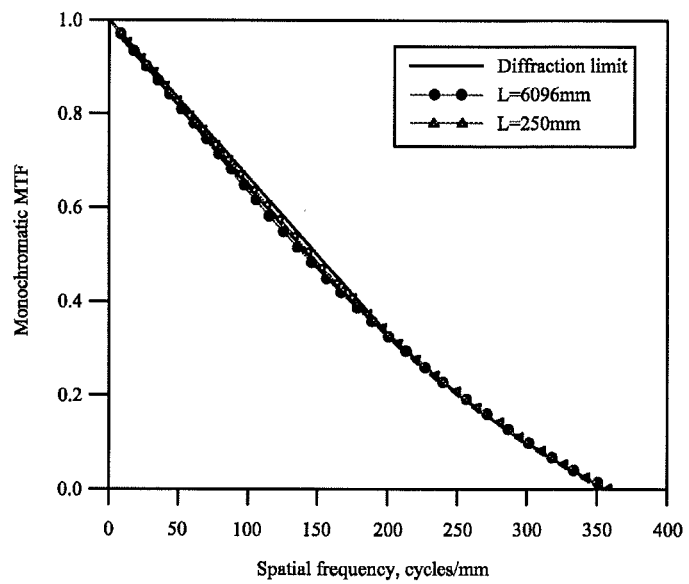
FIG. 3 is a graph of the monochromatic (at $\lambda = 0.543$ μm) average of sagittal and tangential on-axis MTFs for model eye with a 3-mm pupil and the two-element varifocal lens with the following parameters: $A_1 = 0.0124$ mm-2, $R = 7.0181$ mm, $h_1 = 1.0316$ mm, $A_2 = 0.0153$ mm$^{-2}$, $h_2 = 0.358$ mm, $Q_1 = Q_2 = 0$ mm$^{-4}$. The simulated MTFs accommodated to ~6 m (equal to infinity for acuity tests) and 25 cm (at 4 D accommodation) are depicted with solid circles and open triangles, respectively. The AIOL with two cubic optical elements provides near-diffraction-limited performance of the eye in absence of accommodation induced spherical aberration.
Figure 4:
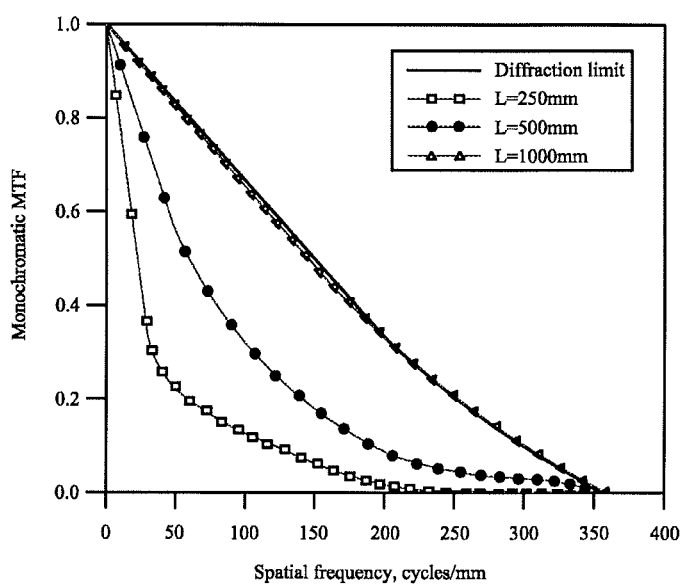
FIG. 4 is a graph of the effect of accommodation induced spherical aberration on performance of the eye in absence of correction of this spherical aberration. In this example, a spherical aberration of −0.03 waves is generated per 1D accommodation. The corresponding monochromatic on-axis MTFs are presented for the model eye implanted with the AIOL with two cubic elements lens accommodated at 25 cm, 50 cm and 1 m, and vision at near distances is degraded leading to loss of sharpness, contrast and detail.
Figure 5:
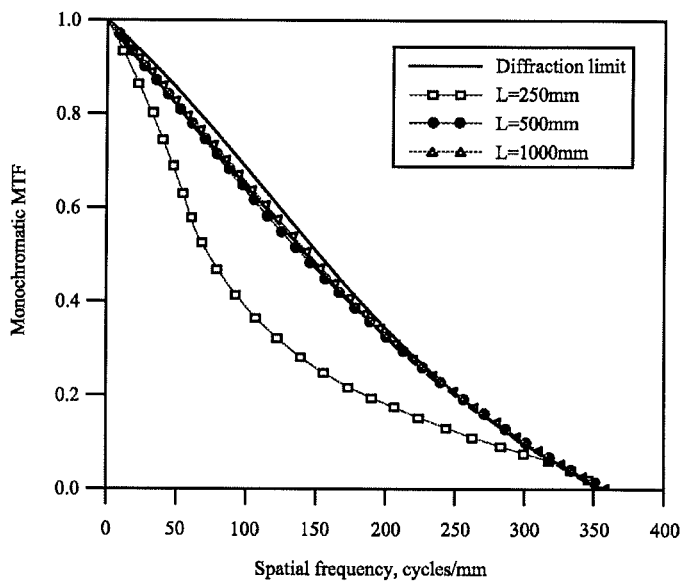
FIG. 5 is a graph of the results when the accommodation induced spherical aberration is corrected for additional fifth order surfaces for variable correction of spherical aberration to the cubic optical elements. In this example, the fifth-order correcting parameter was found to be $Q_1 = Q_2 = 1.313 \times 10^{-4}$ mm$_{-4}$. The monochromatic on-axis MTFs of the model eye with the two-element ophthalmic lens correcting spherical aberration simultaneously with accommodation are shown for the eye accommodated to 25 cm, 50 cm and 1 m.
Figure 6:
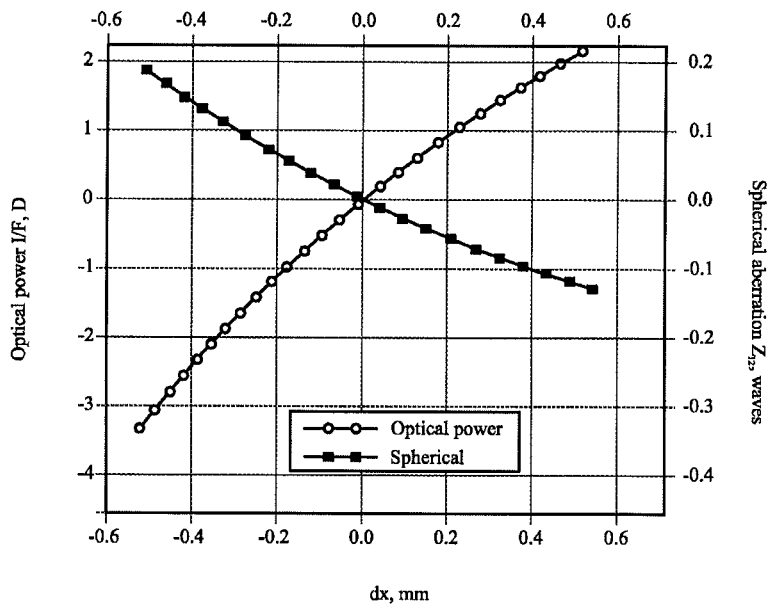
FIG. 6 is a graph of the relationship of accommodation status of the AIOL with shifting cubic elements with variable focus/defocus and variable correction of spherical aberration and degree of correction of spherical aberration.

In this disclosure we introduce and describe optical elements which realize variable correction of higher-order aberrations in combination with variable focus. Simultaneous correction of different-order aberrations is achieved by amending the shape of cubic elements. The variable lenses for AIOLs can include variable correctors which affect various higher-order aberrations simultaneously. Thus these AIOLs can be defined as AIOLs with variable Zernike correctors for correction of variable accommodation-dependent aberrations.

The cornea is considered to be one of the main sources of accommodation-dependent aberrations. The shape of the cornea changes mainly due to changes in the overall shape of the eye and partly due to increased fluid pressure during the accommodative process. The shape change can be measured by corneal topography for which various measuring apparatus are commercially available. These corneal topographers can measure and define the variations in corneal shape during the accommodation process. The measurement can also be performed on cataract and presbyopic eyes because the accommodation-induced changes in the corneal shape are not related with variations in the natural lens geometry. Aberrations induced during the accommodation process by corneal surfaces can be deducted from the measured corneal shape. With these data, the configuration of the intraocular lens that allows correcting the higher-order aberrations caused by the cornea along with defocus can be determined. This intraocular lens comprises at least two refractive elements with the profiles that combine cubic terms for the verifocal effect and higher-order (anti-derivatives of Zernike polynomials) terms providing correction of Zernike aberration terms.

This disclosure introduces and explains the various concepts in variable control of aberrations in the eye and provides one realistic example of a lens design which variably corrects accommodation induced spherical monochromatic aberration.

For purposes of the present disclosure, all references to Zernike aberrations are as provided by a single-index scheme suggested by VSIA task force (L. N. Thibos et al., and VSIA Standards Taskforce Members, "Standards for Reporting the Optical Aberrations of Eyes," OSA Trends in Optics and Photonics 35, Vision Science and its Applications, V. Lakshminarayanan, ed., [Optical Society of America, Washington, D.C., 2000], pp. 232-244). Table 1 summarizes the polynomials with the radial order up to n=4.

TABLE 1

| n | Common name | Zernike term | Mathematical expression |
|---|---|---|---|
| 0 | Piston/bias | $Z_0$ | 1 |
| 1 | Tip/tilt | $Z_1$, tilt y | $2\rho\sin\vartheta$ |
|   |   | $Z_2$, tilt x | $2\rho\cos\vartheta$ |
| 2 | Astigmatism, defocus | $Z_3$, astigmatism y | $\sqrt{6}\rho^2 \sin 2\vartheta$ |
|   |   | $Z_4$, defocus | $\sqrt{3}(2\rho^2 - 1)$ |
|   |   | $Z_5$, astigmatism x | $\sqrt{6}\rho^2 \cos 2\vartheta$ |
| 3 | Coma, trefoil | $Z_6$, trefoil y | $\sqrt{8}\rho^3 \sin 3\vartheta$ |
|   |   | $Z_7$, coma y | $\sqrt{8}(3\rho^3 - 2\rho^2)\sin\vartheta$ |
|   |   | $Z_8$, coma x | $\sqrt{8}(3\rho^3 - 2\rho^2)\cos\vartheta$ |
|   |   | $Z_9$, trefoil x | $\sqrt{8}\rho^3 \cos 3\vartheta$ |
| 4 | Quadrafoil, secondary astigmatism, spherical | $Z_{10}$, quadrafoil y | $\sqrt{10}\rho^4 \sin 4\vartheta$ |
|   |   | $Z_{11}$, sec. astigmatism y | $\sqrt{10}(4\rho^4 - 3\rho^2)\sin 2\vartheta$ |
|   |   | $Z_{12}$, spherical | $\sqrt{5}(6\rho^4 - 6\rho^2 + 1)$ |
|   |   | $Z_{13}$, sec. astigmatism x | $\sqrt{10}(4\rho^4 - 3\rho^2)\cos 2\vartheta$ |
|   |   | $Z_{14}$, quadrafoil x | $\sqrt{10}\rho^4 \cos 4\vartheta$ |

Note that this table can be extended to numerous higher-order polynomials and that the principles outlined in this disclosure apply to all Zernike aberrations.

Aside from the second-order aberration terms, i.e., defocus and astigmatisms, the human eye can have a number of higher-order aberrations (trefoils, comas, spherical aberration etc.) of which spherical aberration is the most profound in practice and which aberration is well documented to vary in accordance with the accommodation status of the eye. For an example and quantification of such variable accommodation induced aberration, we refer to H. Cheng et al. (A population study on changes in wave aberrations with accommodation, J. Vis. 3, 272-280, 2004). This study also provided the basic data for the example described hereinbelow.

During the accommodation process, the optical parameters of various elements of the eye change in combination with a change in the sizes and overall shape of the eye. These changes can induce variable aberrations which can decrease or increase depending on an individual during the accommodative process. Spherical aberration. $Z_{12}$, for example, shows the greatest change in amplitude with accommodation that is approximately 0.06 waves for an accommodation of 1 diopter (D) of a 5-mm pupil of the eye, measured at a wavelength of 0.83 μm. The higher-order ocular contributions can cause significant degradation in imaging quality and are generally considered to have fixed values. Conventional bespoke spectacles can only compensate for the second-order terms defocus and astigmatism.

An inherent advantage of IOLs which allow simultaneous correction of higher-order aberrations together with defocus is their insensitivity to the pupil position and its size. The variable IOLs based on cubic optical elements described in this disclosure will provide correction of ocular aberrations irrespective of the pupil position and size, in contrast to correcting phase plates or ophthalmic lenses utilizing the refractive surfaces of an order higher than two in terms of Zernike aberrations.

The eye has several refractive surfaces which determine its optical properties of which the most important are the anterior and posterior surfaces of the cornea and the anterior and posterior surfaces of the crystalline lens. During accommodation, the shape of the cornea changes to a steepened and flattened corneal curvature. In addition, a change in the shape of the crystalline lens also contributes to the change in the ocular aberrations. In the example of an IOL, the cornea remains the main factor for accommodation-induced aberrations because the crystalline lens is removed from the eye prior to implantation of an IOL. To date no IOL design has, or is likely to have, properties which can realistically correct for these variable aberrations. The present disclosure describes how monochromatic aberrations of different orders can be simultaneously corrected in an AIOL with two shifting cubic optical elements. So the IOL, with a two-element shifting optics with the element shaped as described in the present disclosure, will not only provide variable focus/defocus to restore accommodation of the eye but also variable correction of higher-order ocular aberrations which are aberrations induced by the accommodation process.

It should be noted that such lenses with two cubic optical elements can correct for astigmatic aberrations without additional surfaces or changes in or additions to the basic formulas to which the cubic elements are shaped. Shifting the elements in the y direction will cause astigmatism to occur. By choosing the correct combination of shift in the x (focus/defocus) direction and y (astigmatism) direction, one can control the level of astigmatic aberration and focus/defocus simultaneously. One can, without much difficulty, design an AIOL with cubic optical elements with these elements assembled at an angle between their lines of symmetry in the x direction which precisely controls an astigmatism which varies with the accommodative state of the AIOL. Implantation by surgeons at precise angles is a common practice and was developed for fixed focus IOLs with a fixed astigmatism correction factor.

Accommodation of the human eye results in the change of ocular aberration coefficients. Among all individual Zernike terms, spherical aberration $Z_{12}$ shows the greatest change with accommodation (Cheng et al., 2004). The change of spherical aberration is also always negative, whereas other Zernike aberration coefficients have no preferable direction of the change and are conditioned by the individual features of the human eye.

The present disclosure provides methods for simultaneous correction of the accommodation-dependent corneal aberrations by the intraocular ophthalmic lens which comprises varifocal effect and variable correction of higher-order aberrations and consists of at least two movable optical elements.

The present disclosure provides an accommodating intraocular lens with variable optical power, comprising at least two optical elements, at least one of which is movable relative to the other in a direction perpendicular to the optical axis, wherein the optical elements have a form resulting in a lens with different optical power at different relative positions of the optical elements. At least two of the optical elements of the lens comprises at least one additional optical correction surface which correction surfaces are adapted for simultaneous variable correction of one or more optical aberrations of the natural eye in which the degree of correction depends on the relative position of the optical elements.

Zernike correcting surfaces are added to at least one optical surface of optical elements of an AIOL with shifting cubic optical elements for simultaneous variable correction of accommodation-induced optical aberrations in which the degree of said Zernike correction depends on the relative position of both optical elements.

The features described in the present disclosure are well suited for correction of aberrations of different orders. However, this optical design is particularly suited for implementation in an accommodating intraocular lens, AIOL, which adaptively corrects for defocus in combination with higher-order aberrations produced by the cornea during the accommodation process. Consequently, one exemplary embodiment of the present disclosure provides a lens of kind referred to hereinabove wherein the lens is adapted for variable focusing and for variable correction of higher-order aberrations of the remaining parts of the human eye.

In principle, the invention is adapted to correct for one single aberrations of any order. According to an exemplary embodiment, however, the corrections surfaces can be adapted to simultaneously correct multiple aberrations of more than one order supplementing variable focal power of the ophthalmic lens. We further describe additional optical surfaces providing simultaneous variable correction of optical aberrations of different orders of which the magnitude of corrective contributions depends on the degree of shift of the optical elements.

An important document in this regard is U.S. Pat. No. 3,583,790 which describes only one particular case of spherical aberration which is corrected using specific "quintic" optical surfaces. U.S. Pat. No. 3,583,790 describes two cubic refracting plates for variable focal power according to U.S. Pat. No. 3,305,294; and thus is described by the following expression $$z = S(x, y) = \frac{A}{2}\left(\frac{x^3}{3} + xy^2\right)$$

to which a correction for spherical aberration is added. The term for spherical aberration contains a non-zero 5-th order term following:

$$x = ay + cy^3 + 3cyz^2 + gy^5 + \frac{10}{3}gy^3z^2 + 5gyz^4 \quad (1)$$

For brevity, Equation 1 can be rewritten as: $x=S(y,z)$, where x, y, z are the Cartesian coordinates.

Assuming that the refractive elements are shifted by $\Delta y$, optical path L of the ray intersecting the first element at $\{y,z\}$ becomes:

$$L = nh_1 + nS(y-\Delta y, z) + h_0 + nh_2 - nS(y+\Delta y, z) \quad (2)$$

where n is the refractive index of the plates material; $h_1$ and $h_2$ are the central thicknesses of the refractive plates; $h_0$ is the central distance between them, and S refers to Equation 1.

Retaining only linear in $\Delta y$ terms, Equation 2 yields:

$$L = (nh_1 + h_0 + nh_2) - 2an\Delta y - 6cn[y^2+z^2]\Delta y - 10gn\{y^2+z^2\}^2\Delta y \quad (3)$$

In terms of the optical path difference (hereinafter referred to as "OPD"), OPD of the ray due to the reciprocal shift $\Delta y$ of plates results in:

$$OPD = (n-1)(h_1+h_2) - 2a(n-1)\Delta y - 6c(n-1)[y^2+z^2]\Delta y - 10g(n-1)\{y^2+z^2\}^2\Delta y \quad (4)$$

From Equation 4, it can be concluded that the invented optical system produces when its parts move laterally by a distance of $\Delta y$:
1. First term, $(n-1)(h_1+h_2)$: a constant factor;
2. Second term, $2a(n-1)\Delta y$: a linear piston phase shift (Zernike term $Z_0$, see Table), with no likely application for optical systems except for phase sensitive devices such as interferometers;
3. Third term, $6c(n-1)\lfloor y^2+z^2\rfloor\Delta y$: a parabolic lens, $Z_4$, with variable power. The focal distance of the lens in this exemplary embodiment is $F=[12c(n-1)\Delta y]^{-1}$ and coincides with those obtained in U.S. Pat. No. 3,305,294 when $A=3c$;
4. Fourth term, $10g(n-1)\{y^2+z^2\}^2\Delta y$: a quadric term, $Z_{12}$, third-order spherical aberration linearly changing with $\Delta y$.

The amplitude of spherical aberration is: $A_{12}=10g(n-1)\Delta/\lambda$ where $\lambda$ is the wavelength of light.

It can be concluded that the parabolic, $Z_4$, and quadric terms, $Z_{12}$, in Equation 4 vary linearly with $\Delta y$. Thus, the amplitudes of defocus and spherical aberration are intrinsically interrelated. So, the optical element using a tandem pair of the quintic phase plates as given by Equation 1 is a narrow subclass of two-element varifocal Alvarez lenses as described in U.S. Pat. No. 3,305,294 and this optical system is a varifocal lens which additionally generates spherical aberration that linearly follows $\Delta y$. Such an optical element has a very specific range of applications where defocus and spherical aberration should be changed simultaneously.

In this disclosure, a variable correction of a given aberration or simultaneous correction of many aberrations with specified weights is described. The aberration amplitudes vary with the lateral shift $\Delta x$ and their relative weights can be adjusted as required.

An example for variable correction of spherical aberration is provided hereinbelow.

Experimental studies have shown a nearly linear dependence between accommodation and the amplitude of spherical aberration of the human eye. The variation of spherical aberration is always negative in accommodation and the variation decreases on average ~0.06 waves at a 1-D accommodation of the eye. This may lead to a spherical aberration of ~0.3 waves at a 4-D accommodation which seriously distorts near vision. However, this accommodation induced spherical aberration is likely to be generated by the optical components of the eye, i.e., the cornea, the lens and the vitreous with an unknown component dependent on mechanical deformation of the eye which occurs during accommodation. Near vision is expected to be significantly improved if the accommodation-induced spherical aberration is corrected along with the defocus which is needed for sharpness at near vision.

Yet another exemplary embodiment provides that the lens is adapted to correct variable optical aberrations of the human eye caused by changing of the shape of the cornea due to accommodation.

It should be noted that higher-order aberrations, such as comas, trefoils etc., can also be dependent on the degree of accommodation of the eye. Variable correction of spherical aberration is the main topic of the present disclosure and it is used as an illustration of the developed optical and mathematical principles. Similar optical principles can be applied to basically all higher-order aberrations, and a person skilled in the art will conclude that the optical and mathematical principles set forth in this disclosure using spherical aberration as an example can also be equally applied to correct for increasingly higher-order accommodation-induced optical aberrations. Firstly, aberrations can be corrected in a fixed manner by preshaping a two-element varifocal lens, and we will use an AIOL as an example for such fixed corrections:

The surfaces of the accommodating optical elements are typically shaped according to the Alvarez varifocal lens principle (disclosed in U.S. Pat. No. 3,305,294) that are specified by $$z = S(x, y) = \frac{A}{2}\left(\frac{x^3}{3} + xy^2\right)$$

in which the constant A is adjusted for the use of the lens as an AIOL. A fixed parabolic lens can be added to this accommodating surface to correct for the basic refraction of the human eye. For example, such AIOL can be designed in practice providing, for example, a fixed +22 D refractive power to which an accommodative power of 0-4 D can be added for accommodation. The basic refraction of the eye can be corrected for with a parabolic lens of a fixed optical power with a sag given by $$z = S(x, y) = \frac{A}{2}\left(\frac{x^3}{3} + xy^2\right).$$

The focal power of the additional parabolic lens is $2C(n-1)$, where n is the refractive index of the material. In the general case, the corneal aberrations of the eye can be corrected by refractive surfaces of the variable IOL shaped according to:

$$z = S(x, y) = S_A(x, y) + \frac{r^2}{R\left\{1 + \sqrt{1 - (1+k) \times (r/R)^2}\right\}} + a_1 r^4 + a_2 r^6 + \ldots + a_n r^{(2n+2)} \quad (5)$$

where, $r=\sqrt{x^2+y^2}$; R is the radius of curvature; k is the conic parameter that specifies the type of conicoid; $a_n$ is the $(2n+2)$-th order polynomial coefficient which is, in most cases, $n \leq 2$. In this formula, the simultaneous use of the conic constant and polynomial series is somewhat redundant but has no effect on the operation of the lens. Such an additional surface provides a correction of fixed value, and this correction is independent of the variable defocus of the lens. This approach expands the principles described in U.S. Pat. Nos. 6,609,793 and 6,705,729 for fixed correction of aberrations in (standard and of fixed focus) IOLs which both describe several aspects of such fixed corrections, in particular, the a1 r4+a2 r6 term for correction of single monofocal IOLs. In this disclosure we describe a varifocal lens with additional variable Zernike terms of which the degree of correction changes along with defocus. In the case of complementary configuration variable third- and higher-order aberrations, expressed in terms of Zernike polynomials, as well as their linear combinations are generated having amplitudes changing linearly with the lateral shift $\Delta x$. The following base sag function $S(x,y)$ should be used:

$$z = S(x, y) = \frac{A}{2}\left(\frac{x^3}{3} + xy^2\right) + \frac{1}{2} \int \sum_q C_q Z_q(x, y) dx \quad (6)$$

where P is the constant (in this example, ½), $C_q$ is the modal coefficient corresponding to the q-th Zernike aberration term. Assuming that the elements are made of a material with a refractive index n, the optical path L in the two-element complementary geometry described above, is given by:

$$L = nh_1 + nS(x-\Delta x, y) + h_0 + nh_2 - nS(x+\Delta x, y), \quad (7)$$

In this formula, the constants $h_1$, $h_2$ determine the central thickness of each refractive element, and $h_0$ is the central distance between the respective elements. After simplification, the equation for L yields:

$$L = (nh_1 + h_0 + nh_2) - An(y^2 + z^2)\Delta x - n\Delta x \sum_q C_q Z_q(x, y) + nR(x, y, \Delta x) \quad (8)$$

and the corresponding optical path difference (hereinafter referred to as "OPD") becomes:

$$OPD = (n-1)(h_1 + h_2) - A(n-1)(y^2 + z^2)\Delta x - (n-1)\Delta x \sum_q C_q Z_q(x, y) + (n-1)R(x, y, \Delta x), \quad (9)$$

So, as seen from the derived expression, when the optical parts of the two-element system move laterally by $\Delta x$ each, the system produces:
1. First term, $(n-1)(h_1+h_2)$: a constant piston, $Z_0$;
2. Second term, $A(n-1)(y^2+z^2)\Delta x$: varifocal parabolic lens, $Z_4$. The focal distance of the lens is $F=[2A(n-1)\Delta x]^{-1}$;
3. Third term, $$(n-1)\Delta x \sum_q C_q Z_q(x, y):$$

all aberration terms, $Z_n$, including defocus or linear combination of terms whose amplitudes linearly vary with $\Delta x$, i.e., new amplitudes of aberrations which correspond to $(n-1)\Delta x C_q$. Additional optical power produced by the defocus term $C_4$ is: $F^{-1}=2\sqrt{3}C_4(n-1)\Delta x$, which is expressed in diopters.
4. The last term, $(n-1)R(x,y,\Delta x)$: a contribution of higher-order shift-dependent contributions $\Delta x^3$, $\Delta y^5$, and the like. When $\Delta x \ll 1$, these contributions are negligibly small and can be omitted for practical purposes.

So, a pair of refractive elements, shaped according the base function $S(x,y)$ given above, provides linear change of the specified optical aberrations along with defocus/accommodation for use in AIOLs for treatment of cataracts, presbyopia and spectacle-replacement in general. When applied to AIOLs, we assume that ocular aberrations expressed in terms of Zernike polynomials are accommodation-dependent and associated mainly with the change of the shape of the cornea. Then the ocular aberrations can be corrected simultaneously with defocus by using, e. g., a two-element accommodative IOL with the specified above additional refractive surfaces shaped as $S(x,y)$.

Such AIOL provides a variable defocus of which the focus changes linearly with the lateral shift $\Delta x$. Reciprocal shift of the two refractive elements with the profile $S(x,y)$ specified above by $\Delta x$ in the opposite direction perpendicular to the optical axis results in the linear change of the focusing power $(F^{-1})$ as given by:

$$F^{-1}=2A(n-1)\Delta x+2\sqrt{3}C_4(n-1)\Delta x \quad (10)$$

where A is the amplitude of Alvarez term and $C_4$ is the magnitude of additional defocus.

The modal amplitudes of aberration terms change linearly with shift $\Delta x$. Reciprocal shift of the two refractive elements shaped as $S(x,y)$ by $\Delta x$ in the opposite directions perpendicular to the optical axis results in the linear change of the q-th Zernike aberration term (excluding defocus, i.e. $q \neq 4$). The new modal amplitudes $C'_q$ become:

$$C'_q=(n-1)\Delta x C_q. \quad (11)$$

Correction of defocus results in a simultaneous variation of a linear combination of aberrations. Reciprocal shift of the two refractive elements with the profiles S(x,y), specified above, by Δx in the opposite directions perpendicular to the optical axis gives rise to the linear change of the combination of Zernike aberration terms:

$$z = \sum_q C'_q Z_q(x, y) \quad (12)$$

where the new modal amplitudes are $C'_q=(n-1)\Delta x C_q$. The relative weights of monochromatic aberrations can be adjusted as required by choosing the corresponding coefficients $C_q$.

As an example, simultaneous correction of defocus and spherical aberration in conformity with the principles described above by using a two-element variable lens, as described in International Patent Publication No. WO 2005/084587 and related patents mentioned hereinabove can be accomplished as follows.

Retaining defocus and spherical aberration terms only, the above specified sag function S(x,y) takes the form:

$$z = S(x, y) = \frac{A}{2}\left(\frac{x^3}{3} + xy^2\right) + \frac{B}{2}\int Z_{12}(x, y)dx = $$
$$= \frac{A}{2}\left(\frac{x^3}{3} + xy^2\right) + \frac{B}{2}\sqrt{5}\left\{x - 2x^3 - 6y^2x + \frac{6}{5}x^5 + 4y^2x^3 + 6y^4x\right\} \quad (13)$$

where B is the coefficient of spherical aberration $Z_{12}$. The optical path difference becomes:

$$OPD=(n-1)(h_1+h_2)-A(n-1)(y^2+z^2)\Delta x-B(n-1)\Delta x Z_{12}(x,y)+(n-1)R(x,y,\Delta x) \quad (14)$$

where the residual shift-dependent term R is given by:

$$R(x,y,\Delta x)=-\{A/3+4B\sqrt{5}y^2-2B\sqrt{5}+12B\sqrt{5}x^2\}\Delta x^3-6B\sqrt{5}\Delta x^5/5 \quad (15)$$

The first part in Equation 15 is a combination of defocus ($Z_4$) and astigmatism ($Z_5$) with amplitudes $4B\sqrt{5}\Delta x^3$ and $-4B\sqrt{5}\Delta x^3$, respectively; the last term is a piston ($Z_0$).

The experimental results obtained by Cheng et al. state that a negative spherical aberration of ~0.06 waves is generated on average at a +1-D accommodation of the eye, the two-element accommodative lens specified above by the sag S(x,y) of each element can be implemented to correct spherical aberration. An accommodation of +1-D requires the positive lateral shift $\Delta x_0=[2A(n-1)]^{-1}$. At this shift, the spherical aberration changes by ~−0.06 waves, in other words:

$$\Delta x_0=[2A(n-1)]^{-1} \text{ and finally } B\approx-0.114 A\lambda, \quad (16)$$

where λ represents the wavelength of light.

The final expression for the shape of the refractive elements which can provide for variable correction of both defocus and spherical aberration becomes:

$$z = S(x, y) = \frac{A}{2}\left(\frac{x^3}{3} + xy^2\right) + $$
$$W 2A\lambda\sqrt{5}\left\{x - 2x^3 - 6y^2x + \frac{6}{5}x^5 + 4y^2x^3 + 6y^4x\right\}, \quad (17)$$

W denotes the degree of spherical aberration measured in wavelength units (waves) at a 1-D accommodation or W≅−0.06 waves in the example hereinabove.

All exemplary embodiments described in the present disclosure can also have GRIN and also Fresnel designs in addition to a traditional lens design. GRIN and Fresnel designs allow lenses to be manufactured significantly thinner compared to traditional lenses. The degree of chromatic aberrations can be reduced by Fresnel designs, and GRIN designs offer alternatives with regard to distribution of optical quality over the surface of the optics.

Similarly, as further examples of such variable corrections, the final expression for the shape of the refractive elements which can provide for variable correction of both defocus and astigmatism becomes:

$$z = S(x, y) = \frac{A}{2}\left(\frac{x^3}{3} + xy^2\right) + B\left\{\frac{x^3}{3} - xy\right\}$$

and the final expression for the shape of the refractive elements which can provide for variable correction of both defocus and a coma becomes:

$$z = S(x, y) = \frac{A}{2}\left(\frac{x^3}{3} + xy^2\right) + C\left\{\frac{3}{4}x^4 + \frac{3}{2}x^2y^2 - x^2\right\}.$$

Note that, in practice, correction of the aberrations defocus, spherical aberration, astigmatism and coma will provide the eye with a virtually aberration-free vision. However, if needed, formulas for correction of all variable corrections can be derived within the framework outlined above.

The present disclosure does not only provide IOLs as described hereinabove, but also provides a method for applying such lenses. In this respect, it is noted that the provision of a correction surface adapted to the eye of the person in question requires the measurement of the aberrations of the eye. After the aberrations have been measured, the correction surfaces must be calculated and, subsequently, the optical elements must be made, preferably by a machining process, such as precision lathing.

Note that, in practice, the spherical aberration of the cornea can be measured via various corneal topography measuring apparatus, the AIOL design adapted accordingly; and that the AIOL can be manufactured with precision lathing technologies. It shows that shifting the optical elements by 0.18 mm each provides ~1D of accommodation in combination with a spherical aberration term which decreases by ~0.03 waves. This lens provides a focus/defocus function to the eye as well as a complete correction of accommodation induced spherical aberration.

In this example, the lens (as illustrated in FIG. 1, in the eye, and FIG. 2, as separate schematic) consists of two refractive parts spaced apart by d (0.5 mm, in this example) and the anterior part (with optical axis $Z_1$) is shaped according to:

$$z_1 = S_1(x_1, y_1) = h_1 - \frac{r^2}{R} \frac{1}{1 + \sqrt{1 - \frac{r^2}{R^2}}} - \qquad (18)$$

$$A_1 \left\{ x_1 y_1^2 + \frac{x_1^3}{3} \right\} - \frac{Q_1}{2} \int^{x_1} Z_{12}(x', y_1) dx',$$

where: $r = \sqrt{x_1^2 + y_1^2}$; R is the radius of curvature; $A_1$ is the amplitude of Alvarez term; $Q_1$ is the amplitude of 5th order in x term; h1 is the central thickness of the element. In the present example, $A_1$=0.012 mm-2, R=6.866 mm, $h_1$=1 mm. The back (inner) side of the anterior element is a plane. An explanation of the various terms in this formula is provided hereinabove.

The second, posterior, refractive element has a profile given by:

$$z_2 = S_2(x_2, y_2) = h_2 + A_2 \left\{ x_2 y_2^2 + \frac{x_2^3}{3} \right\} + \frac{Q_2}{2} \int^{x_1} Z_{12}(x', y_1) dx', \qquad (19)$$

where: $A_2$ is the amplitude of Alvarez term; $Q_2$ is the amplitude of the fifth order term in x term; h2 is the central thickness of the element. Parameters were: $A_2$=0.014308 mm-2, $h_2$=0.35 mm. The inner side is a plane. For both elements $Q_1 = Q_2 = -7.1 \times 10^{-5}$ mm$^{-4}$. An explanation of the various terms in this formula is provided hereinabove.

The described lens made of a material with the refractive index n=1.46, provides a focusing power of about +18 D in an aqueous solution (with a refractive index n=1.337) when unaccommodated, i.e., at $\Delta x$=0, and allows changing defocus and spherical aberration.

Correction for a single Zernike term or a combination of terms results in a residual (mostly cubic or more complex) term. A disadvantage of the designs and optical principles is that, in simultaneous correction of many aberrations or correction of an aberration with an order higher then two, e.g., trefoils, comas, spherical aberrations, and the like, using a two-element system, the following base function:

$$z = S(x, y) = \frac{A}{2}\left(\frac{x^3}{3} + xy^2\right) + \frac{1}{2} \int \sum_q C_q Z_q(x, y) dx \qquad (18)$$

the contribution of the residual term non-linearly increases with as given by:

$$R(x, y, \Delta x) = \sum_{p=1} \frac{\Delta x^{2p+1}}{(2p+1)!} \sum_q C_q \frac{\partial^{(2p+1)} Z_q(x, y)}{\partial x^{(2p+1)}} \qquad (19)$$

according to which formula the limitations of correction can be determined in relation to degradation of the resulting image, e.g., on the retina of the human eye. Whether these limitations have been reached is dependent on the application and requirements on the AIOL with variable correction of aberrations.

The reciprocal shift of the two refractive elements with the profile S(x,y) specified above by $\Delta x$ in the opposite directions perpendicular to the optical axis, aside from the monochromatic aberrations $Z_q$, expressed in terms of Zernike polynomials, linearly changing with $\Delta x$, produces the said non-linearly varying residual term determined by Equation 19 with R=0 for the second-order aberrations (i.e., defocus $Z_4$ and astigmatisms $Z_3$, $Z_5$) and R≠0 for higher-order aberrations. In most cases, the lateral shift is small with respect to the system aperture (that is supposed to be unity in the formulae above), so $\Delta x \ll 1$ and the residual term $R \sim O(\Delta x^3)$ becomes negligibly small.

In practice, this residual term could degrade the overall optical quality of the AIOL and one should attempt to find a reasonable compromise between Zernike correction and residual term to maximize correction of Zernike aberrations while reducing the residual term as not to degrade the overall optics performance of the AIOL. Details of such a balance are dependent on the AIOL design at hand.

For purposes of the present disclosure, the term "optical surface" of an optical element means the shape of an actual surface and also includes its "optical properties" and the resulting "optical effects" in addition to a traditional definition of an "optical surface". Usually the lens surface is assumed to be a smooth and homogenious surface shaped according to the model function and fabricated by using, for example, modern advanced precision lathing technologies by which various IOLs and contact lenses are currently manufactured.

With current technologies, similar optical properties can be achieved by using, for example, gradient index (GRIN) optical elements or Fresnel optical designs which can be of a "flat" nature. Other optical technologies to achieve the optical properties for such AIOL, as implied by the optical models described in this disclosure, are considered to be part of this disclosure.

All patents, patent applications and publications referred to herein are incorporated by reference in their entirety.

The invention claimed is:

1. An accommodating intraocular lens with variable optical power, comprising:
   two optical elements, said two optical elements are movable relative to each other in a direction perpendicular to the optical axis,
   wherein the optical elements have such a form as to result in the lens having different optical power at different relative positions of the optical elements with the optical elements each comprising a lens on an accommodation surface having a fixed diopter power,
   wherein each of the optical elements comprises at least one additional optical correction surface which correction surfaces are adapted for simultaneous variable correction of at least one variable optical aberration other than defocus, in which a degree of correction depends linearly on the relative position of the optical elements,
   wherein the combination of fixed diopter powers is distributed over the two optical elements such that the combination of the fixed optical powers is constant regardless of the position of the two optical elements relative to each other,
   wherein said at least one variable optical aberration corrects aberrations caused by shifting of the optical elements in combination with the accommodation-induced aberrations of an eye, and
   wherein each optical element is a single piece.

2. The accommodating intraocular lens of claim 1, wherein the at least one optical correction surface of each of the optical elements satisfies the following formula:

$$z = S(x, y) = \frac{A}{2}\left(\frac{x^3}{3} + xy^2\right) + W2A\lambda\sqrt{5}\left\{x - 2x^3 - 6y^2x + \frac{6}{5}x^5 + 4y^2x^3 + 6y^4x\right\}$$

wherein x, y and z represent distances along x and y axes perpendicular to the optical axis and z represents the distance in the direction of the optical axis, A and W represent the amplitude in the direction of the optical axis to correct variable defocus and variable spherical aberration simultaneously and λ represents the wavelength of visible light.

3. The accommodating intraocular lens of claim 1, wherein the at least one optical correction surface of each of the optical elements satisfies the following formula:

$$z = S(x, y) = \frac{A}{2}\left(\frac{x^3}{3} + xy^2\right) + B\left\{\frac{x^3}{3} - xy\right\}$$

wherein x and y represent distances along x and y axes perpendicular to the optical axis, z represents the distance in the direction of the optical axis, and A and B represent amplitudes in the direction of the optical axis to correct variable defocus and variable astigmatism simultaneously.

4. The accommodating intraocular lens of claim 1, wherein the at least one optical correction surface of each of the optical elements satisfies the following formula:

$$z = S(x, y) = \frac{A}{2}\left(\frac{x^3}{3} + xy^2\right) + C\left\{\frac{3}{4}x^4 + \frac{3}{2}x^2y^2 - x^2\right\}$$

wherein x and y represent distances along x and y axes perpendicular to the optical axis, z represents the distance in the direction of the optical axis, and A and C represent the amplitude in the direction of the optical axis to correct variable defocus and variable coma simultaneously.

* * * * *